United States Patent [19]

O'Neill et al.

[11] Patent Number: 4,924,880

[45] Date of Patent: May 15, 1990

[54] DENTAL ANESTHESIA APPARATUS

[75] Inventors: Michael W. O'Neill, Lakewood; Leon M. Silverstone, Denver; Michael E. Halleck, Longmont, all of Colo.

[73] Assignee: Sion Technology, Inc., Aurora, Colo.

[21] Appl. No.: 272,225

[22] Filed: Nov. 16, 1988

[51] Int. Cl.$^5$ ............................................. A61N 1/00
[52] U.S. Cl. .................................. 128/787; 128/802; 128/419 R
[58] Field of Search .................... 128/419 R, 421, 422, 128/423, 787, 798, 802, 803; 346/33 ME

[56] References Cited

U.S. PATENT DOCUMENTS

| | | | |
|---|---|---|---|
| 4,177,819 | 12/1979 | Kofsky et al. | 128/423 R |
| 4,248,247 | 2/1981 | Ware et al. | 128/798 |
| 4,338,945 | 7/1982 | Kosugi et al. | 128/421 |
| 4,391,278 | 7/1983 | Cahalan et al. | 128/798 |
| 4,503,863 | 3/1985 | Katins | 128/421 |
| 4,509,520 | 4/1985 | Dugot | 128/421 |
| 4,539,996 | 9/1985 | Engel | 128/640 |
| 4,782,837 | 11/1988 | Hogan | 128/421 |
| 4,784,142 | 11/1988 | Liss et al. | 128/419 R |

FOREIGN PATENT DOCUMENTS 0197889  10/1986  European Pat. Off. ............ 128/421

Primary Examiner—Lee S. Cohen
Assistant Examiner—Scott Getzow
Attorney, Agent, or Firm—Harold A. Burdick

[57] ABSTRACT

Apparatus is disclosed for achieving improved dental anesthesia utilizing electronic stimulation applied through electrodes positioned inside the mouth of a patient. Each electrode includes an insulating base of foam material with an adhesive at one side thereof to retain one end of an electrical lead in contact with an electrically conductive elastomer, which elastomer has a surrounding outer layer of adhesive for maintaining the elastomer positioned inside the mouth of a patient. A transcutaneous nerve stimulator is utilized to generate the stimulating output signal, which signal may be a pulsed DC signal, an AC signal, a pulsed DC signal followed by an AC signal, or various other combinations of such signals, and the pulsed DC signal is offset to a fixed quiescent DC level above a zero voltage reference when applied to the patient. A threshold intensity for application of the stimulating output signal may be selected at the main unit of the apparatus by the operator, and increases in intensity of the stimulating output signal may be controlled remotely from the main unit by the patient, with the selected intensity being displayed at the main unit both digitally and by a bar graph.

25 Claims, 7 Drawing Sheets

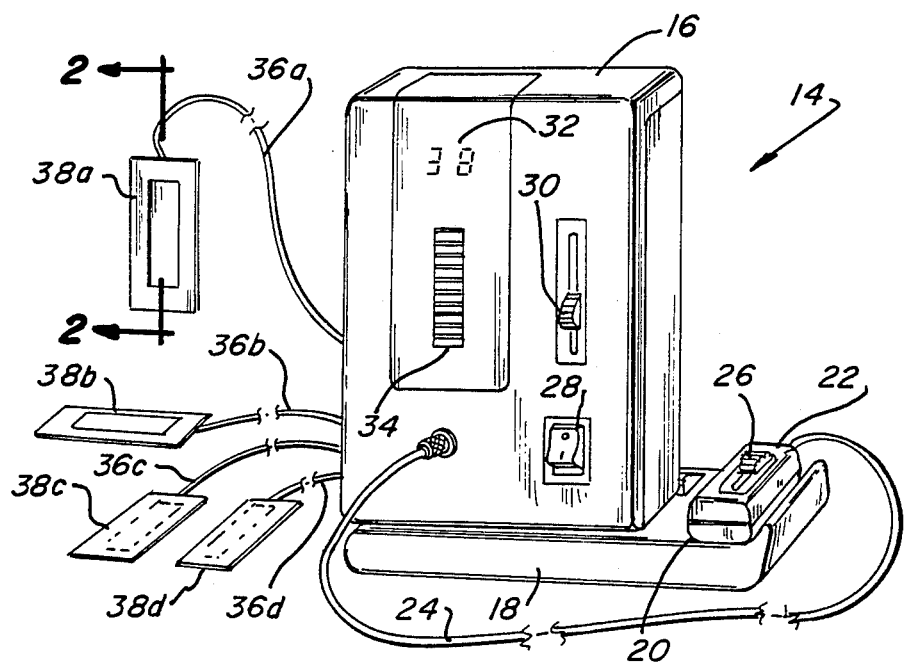
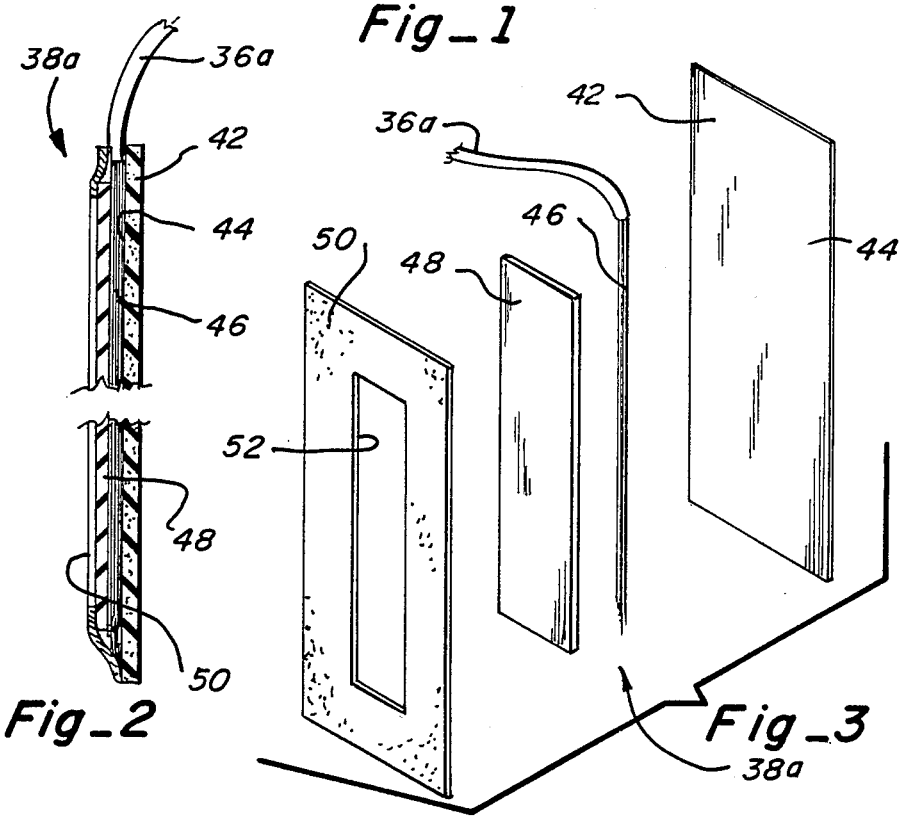

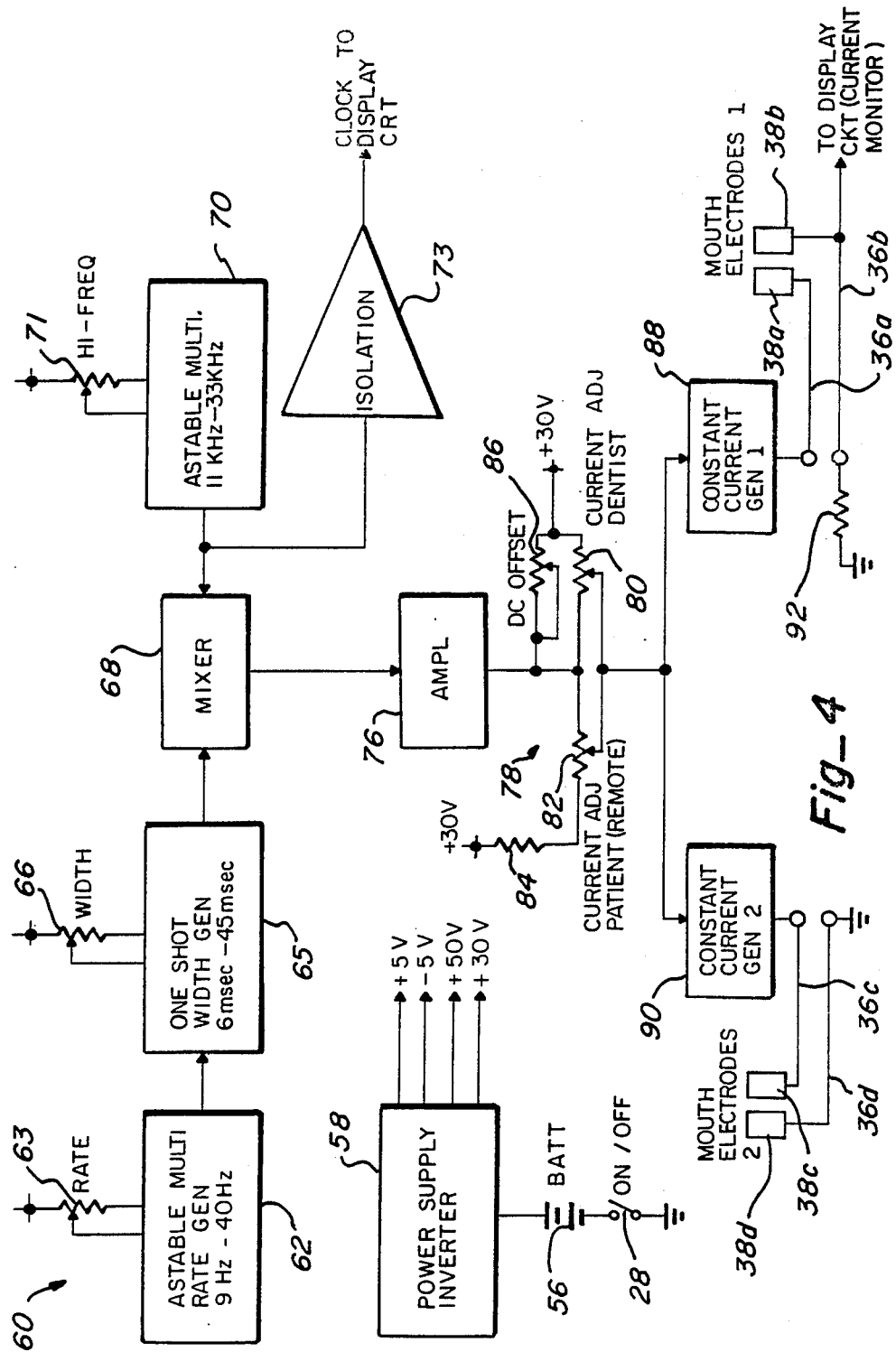
Fig_4

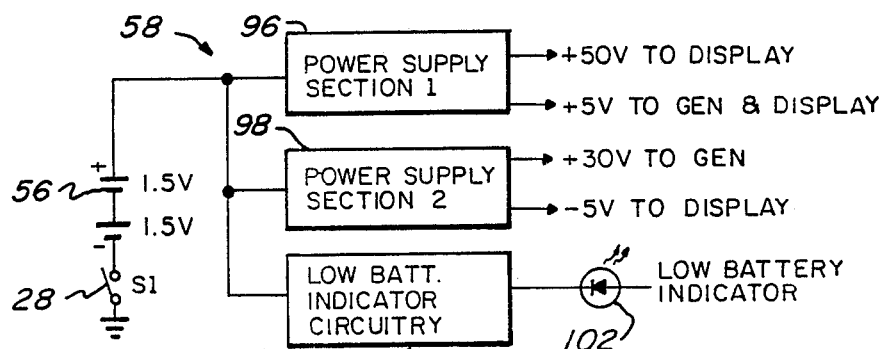
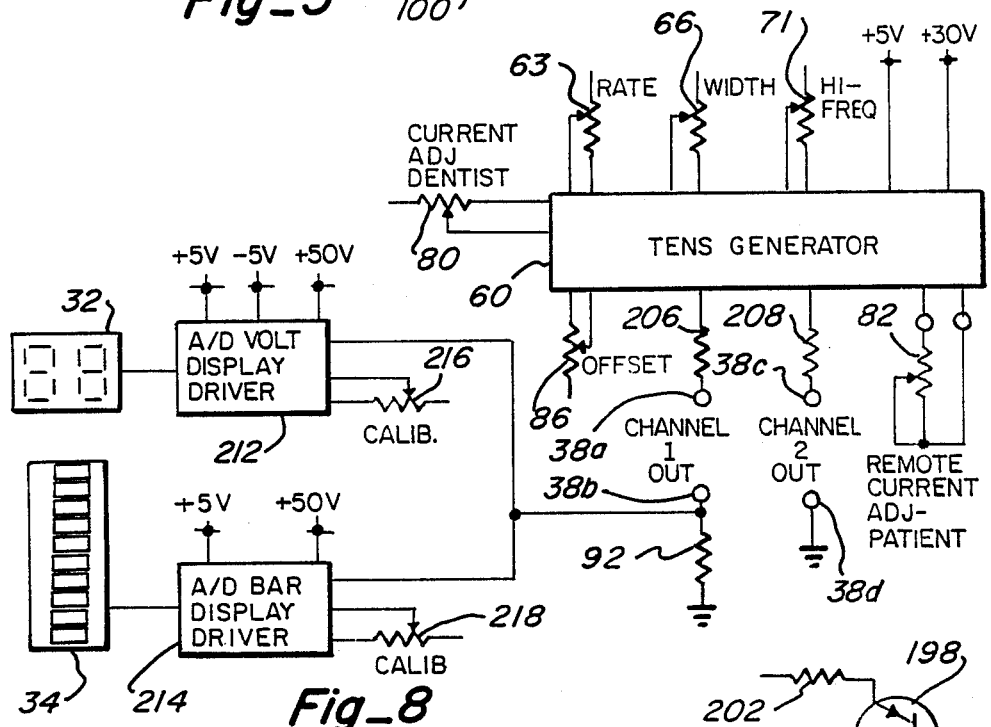
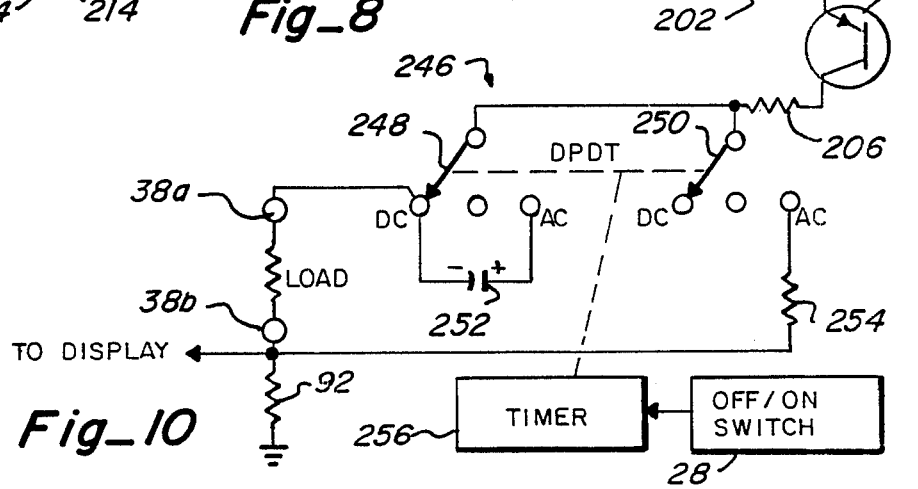

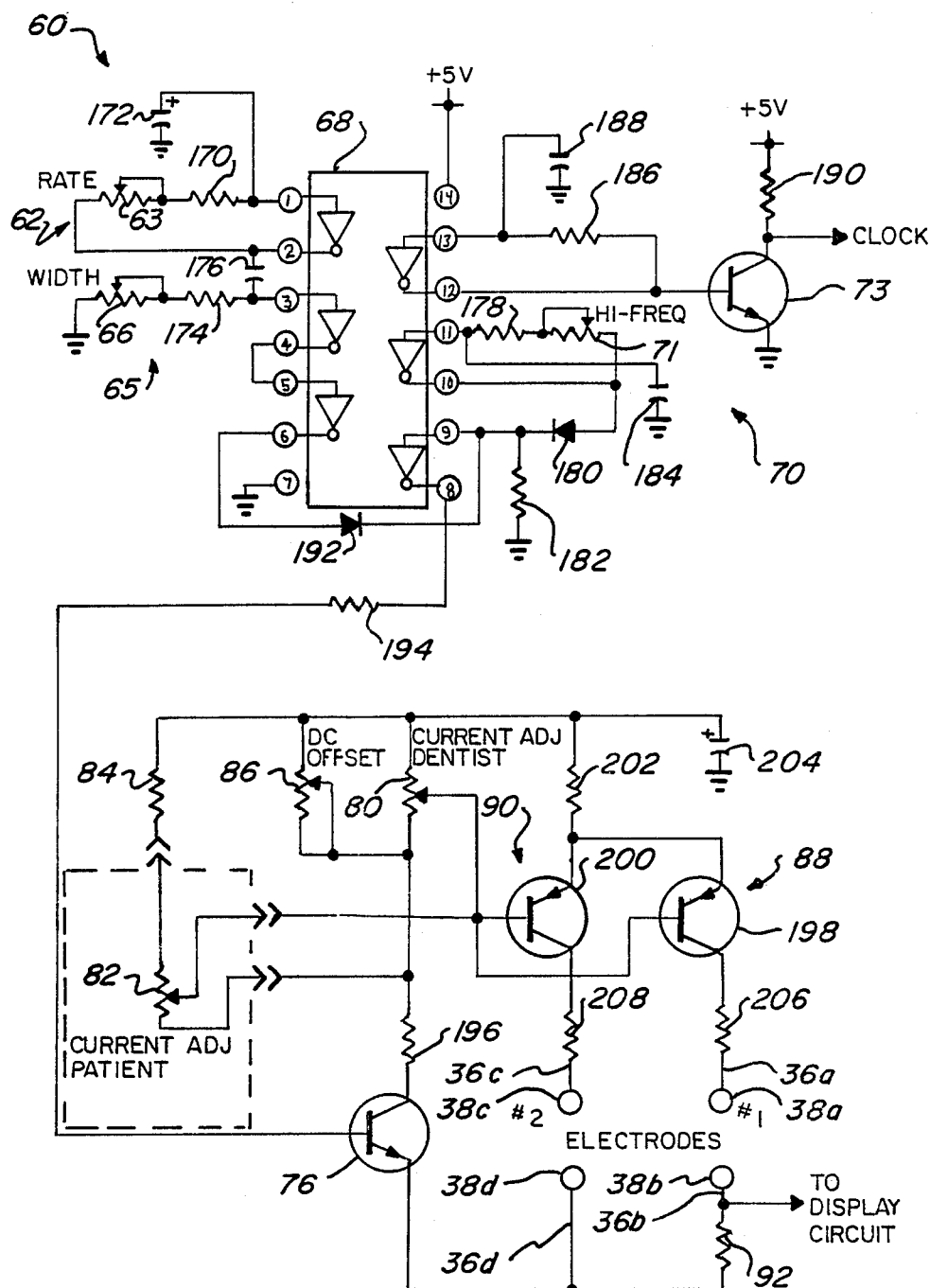
Fig_7

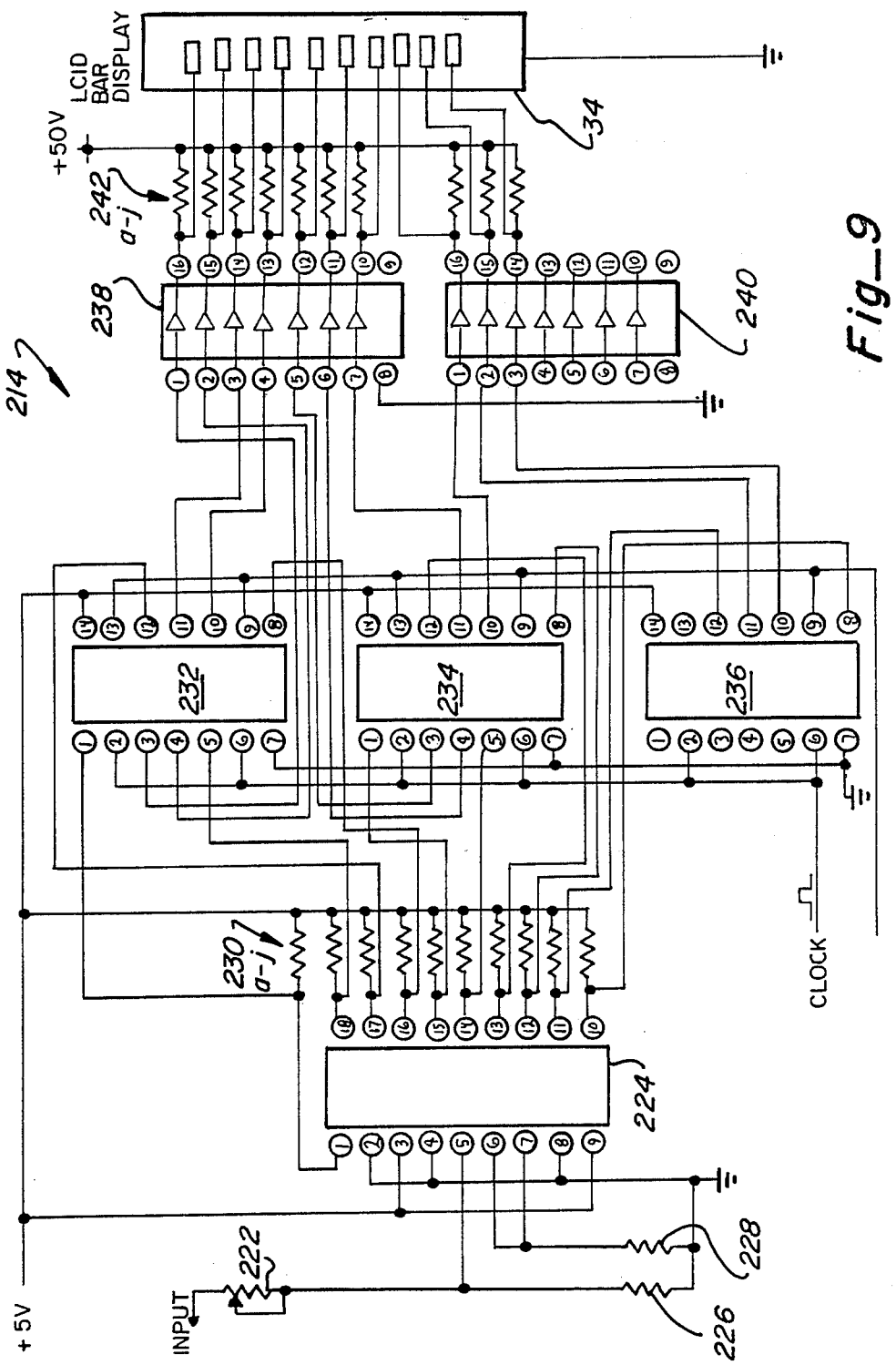
Fig_9

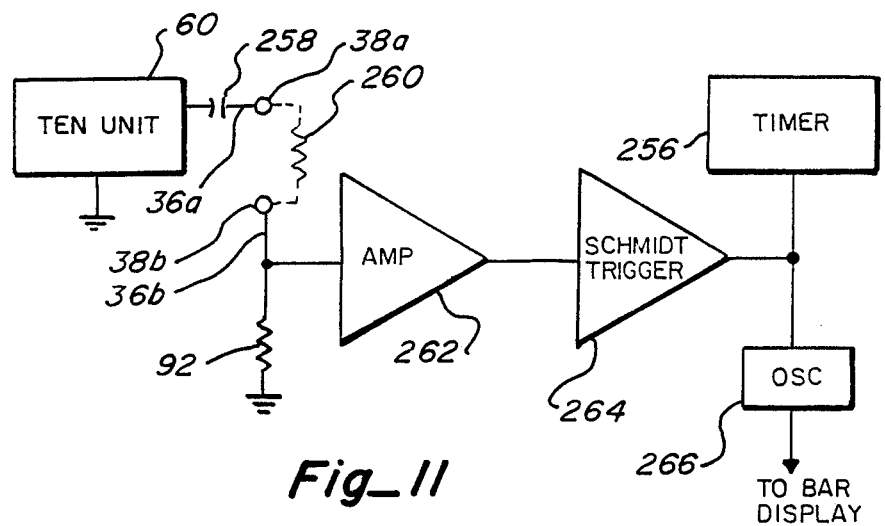
Fig_11
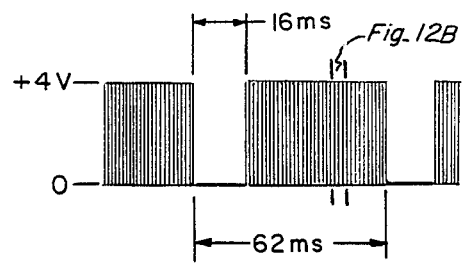
Fig_12A
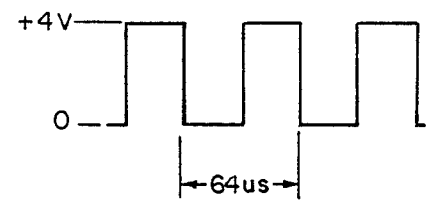
Fig_12B
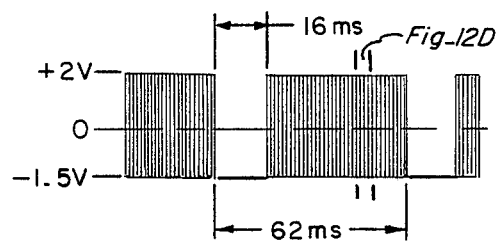
Fig_12C
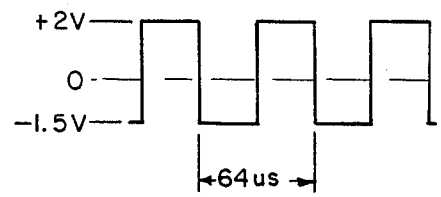
Fig_12D

4,924,880

DENTAL ANESTHESIA APPARATUS

FIELD OF THE INVENTION

This invention relates to dental anesthesia apparatus, and, more particularly, relates to an electronic device for applying electrical signals through electrodes positioned inside the mouth of a patient to effect dental anesthesia.

BACKGROUND OF THE INVENTION

It is oftentimes necessary, or at least desirable, to provide an anesthetic to a patient prior to performing at least some types of dental work on that patient. In the past, such anesthesia has commonly been accomplished by use of a local anesthetic injected through a needle inserted to, or adjacent to the gum of the patient.

More recently, electronic stimulation has been suggested for use in providing dental anesthesia (see, for example, U.S. Pat. No. 4,550,733), and it has been suggested that the intensity of application of such electrical stimulation can be remotely controlled by the patient (see, for example, U.S. Pat. No. 4,676,257).

It is felt, however, that further improvement in dental anesthesia apparatus could be effectively utilized.

SUMMARY OF THE INVENTION

This invention provides an improved dental anesthesia apparatus that includes an electronic stimulator that is connected with electrodes to provide a stimulating signal inside the mouth of a patient to preclude the feeling of pain by the patient while dental work is being performed on the patient.

The stimulation is in the form of a pulsed DC signal, an AC signal, or pulsed DC signal followed by an AC signal, with the pulsed DC signal, when utilized, being offset to a fixed quiescent level above a zero volt level to improve the anesthetic effect and with application of the pulsed DC signal followed by application of the AC signal being timewise controlled manually or automatically. A first intensity level control is positioned at the main unit of the apparatus for use by the operator, such as the dentist, for example, and a second intensity level control is positioned remote from the main unit for use by the patient so that, for example, the threshold intensity can be selected by the dentist and the patient can thereafter increase the intensity level above the dentist selected threshold level. Readily viewable digital and bar graph displays of the intensity level selected are also provided.

Each electrode includes an insulating base, preferably of foam material, having an adhesive on one side thereof to retain one end of the associated electrical lead in contact with an electrical conductor, preferably an elastomer, which conductor has a surrounding adhesive layer capable of releasably maintaining the conductor positioned inside the mouth of the patient.

It is therefore an object of this invention to provide an improved dental anesthesia apparatus.

It is another object of this invention to provide an improved apparatus that includes an electronic stimulator providing an electrical signal through electrodes positioned inside the mouth of a patient to effect dental anesthesia.

It is still another object of this invention to provide an improved dental anesthesia apparatus that includes an electronic stimulator having a first intensity level control for allowing intensity selection by the operator at the main unit of the apparatus and a second intensity level control for allowing intensity selection by a patient remote from the main unit.

It is another object of this invention to provide an improved dental anesthesia apparatus that includes an electrical stimulator for providing pulsed DC output signal, an AC output signal or a pulsed DC output signal followed by an AC output signal, with the pulsed DC output signal, when utilized, being offset to a fixed quiescent level above zero volts, and with the application of the pulsed DC output signal followed by application of the AC output signal being timewise controlled.

It is still another object of this invention to provide an improved dental anesthesia apparatus that includes an electrode having an insulating base with an adhesive on one side thereof to maintain one end of an electrical lead in contact with an electrically conductive element, which element has a second adhesive capable of maintaining the element positioned inside the mouth of a patient.

With these and other objects in view, which will become apparent to one skilled in the art as the description proceeds, this invention resides in the novel construction, combination, and arrangement of parts substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which:

FIG. 1 is a perspective view of the apparatus of this invention;

FIG. 2 is a cut-away side view taken through lines 2—2 of FIG. 1;

FIG. 3 is an exploded view of the electrode shown in FIG. 2;

FIG. 4 is a block diagram of the electrical circuitry of the apparatus shown in FIG. 1;

FIG. 5 is a block diagram of the power supply utilized in this apparatus;

FIG. 7 is an electronic schematic diagram of the apparatus other than the power supply shown in block form in FIG. 4;

FIG. 8 is a block diagram illustrating the display unit utilized in this apparatus;

FIG. 9 is an electrical schematic diagram of the bar graph display circuitry shown in block form in FIG. 8;

FIG. 10 is an electrical schematic diagram illustrating switching of the output signal between AC and pulsed DC;

FIG. 11 is a simplified circuit illustrating electronic stimulator output into a 1000 $\mu$ test load, and also illustrating automatic timewise safety circuitry for conducting automatic timewise actuation and displaying electrode associated error;

FIG. 12A is a typical waveform illustrating a pulsed DC output utilizing the simplified circuitry of FIG. 11;

FIG. 12B is an enlarged portion of the waveform shown in FIG. 12A;

FIG. 12C is a typical waveform illustrating an AC output utilizing the simplified circuitry of FIG. 11; and FIG. 12D is an enlarged portion of the waveform shown in FIG. 12C.

DESCRIPTION OF THE INVENTION

Figure 6:
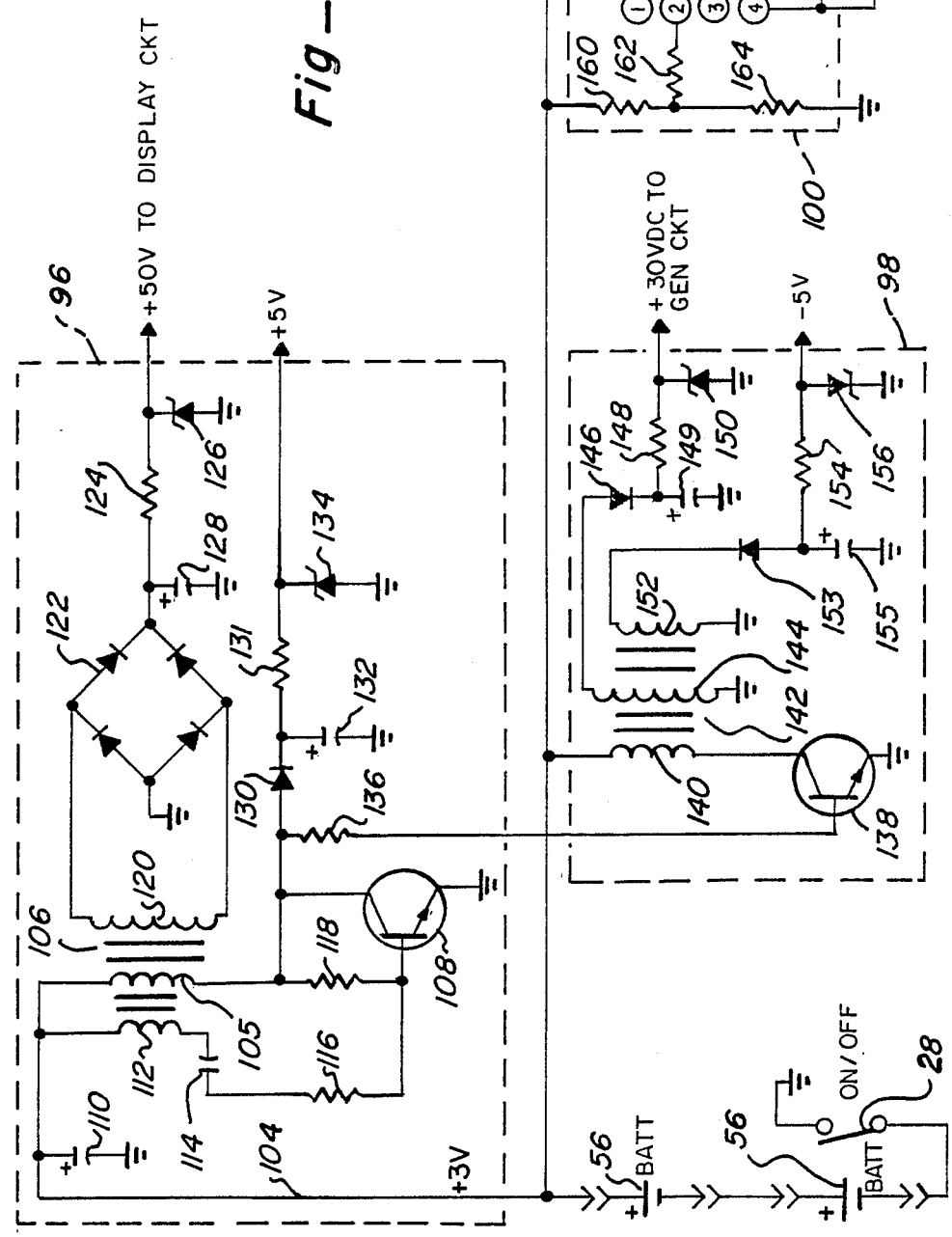
FIG. 6 is an electronic schematic diagram of the power supply shown in block form in FIG. 5.

The apparatus 14 of this invention is shown in FIG. 1 to include a main unit 16 having the electronic circuitry of the apparatus therein. As shown in FIG. 1, a base 18 is preferably provided for positioning of unit 16 thereon, and base 18 also has a ledge 20 therein for receiving remote controller 22 when not being utilized by a patient remote from main unit 16. Remote controller 22 is connected to unit 16 by means of electrical lead 24, and remote controller 22 has an intensity level control actuator 26 thereon to normally allow a patient to remotely select a desired level of intensity.

As also illustrated in FIG. 1, unit 16 has an off/on switch 28 at the front face thereof and intensity level control actuator 30 to be normally operated by an operator (such as a dentist or other user). A digital display 32 and a bar graph display 34 are also provided to indicate the intensity then selected.

For application of the electronic signal to a patient to effect dental anesthesia of that patient, a plurality of jacks (or other conventional connectors) (not shown) are provided at the rear face of the unit, which jacks receive, for example, standard plugs which are electrically connected through leads 36a–d to a plurality of electrodes 38a–d. Four electrodes are shown herein for use with a dual channel device, but it is to be appreciated that a single channel could be utilized requiring only two leads and two associated electrodes.

Electrodes 38a–d may be identical and are configured in such a way as to be held in place inside the mouth of a patient (usually at the gum of the patient, as by being self-adhering to the gum, for example) to allow effective electronic dental anesthesia of the patient.

Electrode 38a is illustrated as an example of electrode configuration (the remainder of the electrodes are preferably of like configuration although dimensions may be varied as needed) in FIGS. 2 and 3. As shown, electrode 38a includes an insulating base 42 (preferably of foam material, which foam material may be, for example, a polyethylene foam) having an adhesive 44 (such as, for example a medical grade adhesive) on the inner side thereof. The associated electrical lead, or wire, 36a, has the normal insulation thereon removed at the free end 46 and the free end of the wire is positioned centrally on insulating base 42 and maintained in the selected position by adhesive 44. An electrically conductive element 48 (preferably an electrically conductive elastomer, which elastomer may be, for example, carbon impregnated silicone), having dimensions smaller than that of insulating base 42, is positioned over free end 46 of the wire and likewise is held in position by adhesive 44 on insulating base 42.

Adhesive layer 50 (such as, for example, a hydrophilic FDA ingredient approved adhesive), having dimensions slightly larger than that of insulating base 42, has a central notch 52 therein, and adhesive layer 50 is maintained in the desired position by adhesive 44 on insulating base 42 so that adhesive layer 50 effectively surrounds elastomer 48 so that elastomer 48 extends through notch 52.

In a working embodiment of the electrodes of the invention, the insulating base utilized was a medical foam known as DEV-7298, the adhesive was MA-24, the elastomer was carbon impregnated silicone, and the hydrophilic adhesive was known as Wetstick, with all of the foregoing being commonly available from Adhesives Research, Inc.

The outer side of adhesive layer 50 (i.e., the side facing away from insulating base 42) must be capable of adhering to a wet surface such as commonly found inside the mouth of a patient so that adhesive layer 50 releasably maintains the elastomer in position in contact with the desired portion (for example, the gum) inside the mouth of the patient. By this arrangement, the stimulating signal generated by the stimulating unit is coupled to the electrodes and directly applied to the desired portion inside the mouth of the patient to preclude the feeling of pain by the patient during dental or other work inside the mouth of the patient.

It is meant to be realized that the electrode materials, configurations and/or dimensions illustrated could be varied as needed for a particular application so long as the stimulating signal is directly delivered through an electrode in contact with a body portion within the mouth (such as the gum) with the electrode preferably being releasably maintained in position by an adhesive also contacting the body portion.

The electronic circuitry of apparatus 14 is shown in block form in FIG. 4. As shown, power for the unit is supplied by batteries 56 (which are also positioned inside unit 16), and application of power is controlled by off/on switch 28. With switch 28 in the on, or closed, position, the voltage from batteries 56 is coupled to power supply inverter 58 which supplies the necessary voltages to the various portions of the unit for operation.

As also shown in FIG. 4, signal generating portion 60 of the device (which may be a transcutaneous nerve stimulator) includes rate generator 62, which generator is preferably an astable multivibrator, that provides an output signal, the rate of which is adjustable by potentiometer 63 between about 9 Hz and 40 Hz (for example adjustable between 0 and 50 K$\Omega$). The output signal from rate generator 62 is coupled to width generator 65, which generator is preferably a one-shot multivibrator, that provides an output signal the width of which is adjustable by potentiometer 66 between about 6 milliseconds and 45 milliseconds (for example adjustable between 0 and 50 K$\Omega$).

The output signal from width generator 65 is coupled as one input to mixer 68 (for example a Z4L14), which mixer receives a second input from high frequency generator 70, which generator is preferably an astable multivibrator, the frequency of which is adjustable by potentiometer 71 between 11 kilohertz and 33 kilohertz (for example adjustable between 0 and 50 K$\Omega$). The output of high frequency generator 70 is also coupled through isolation amplifier 73 as a clock signal to the display circuit.

The output from mixer 68 is coupled through amplifier 76 to current selection circuitry 78, and, more particularly, to potentiometers 80 and 82 (with potentiometer 82 having a resistor 84 in series therewith) and variable resistor 86 (potentiometers 80 and 82 and variable resistor 86 being adjustable for example, between 0 and 50 K$\Omega$). The wiper of potentiometer 80 is controlled by actuator 30 at unit 16 (for actuation by the operator to set, for example, the threshold current intensity to be delivered by the apparatus). The wiper of potentiometer 82 is controlled by actuator 26 at remote controller 22 (for actuation remotely by a patient to set, for example, the current intensity above the threshold as established by the operator).

As indicated in FIG. 4, potentiometer 80 is connected to the +30 volt power supply and potentiometer 82 is connected with the +30 volt power supply through resistor 84. In addition, variable resistor 86 is connected between the +30 volt power supply and amplifier 76 to establish a fixed quiescent DC level that is offset from zero voltage (while such DC signal offset is illustrated herein, it is felt that a DC offset in the AC signal, as hereinafter described, could also be beneficially utilized, for example in a range from less than one mA to two mA).

The wipers, or taps, of potentiometers 80 and 82 are commonly electrically connected to constant current generators 88 and 90 (for dual channel operation, it being realized, however, that only one constant current generator would be needed and utilized if only one set of two electrodes are to be utilized). The output from constant current generator 88 is coupled through lead 36a to electrode 38a with electrode 38b being connected with ground through lead 36b and resistor 92 (lead 36b is also connected with the display circuitry). In like manner, the output from constant current generator 90 is coupled through lead 36c to electrode 38c, with electrode 38d being connected with ground through lead 36d.

Power supply inverter 58 is shown in block form in FIG. 5. As shown, when switch 28 in the on, or closed, position, power from batteries 56 is applied to power supply sections 96 and 98 (power supply 96 supplies +50 volt power to the display and +5 volt power to the stimulation unit and display, while power supply 98 supplies +30 volt power to the transcutaneous nerve stimulator and −5 volt power to the display). In addition, power from batteries 56 is also supplied to low battery indicator circuitry 100, the output of which is displayed by low power indicator 102 (which indicator may be a separate light emitting device (LED) 102, as indicated in FIG. 5, or digital display 32 may be utilized to indicate low power).

Power supply inverter 58 is shown in greater detail in FIG. 6. As shown, the power from batteries 56 (+3 volts) is coupled on lead 104 to one side of primary winding 105 (7 turns) of transformer 106, with the other side of primary winding 105 being connected to the collector of transistor 108. Lead 104 also has bypass capacitor 110 to ground connected thereto, as is two-turn winding 112, which winding is connected to the base of transistor 108 through series connected capacitor 114 and resistor 116 (the base and collector of transistor 108 are also connected through resistor 118). Secondary winding 120 (150 turns) of transformer 106 is connected to bridge rectifier 122, with the output from rectifier 122 being the +50 volt output that is coupled through resistor 124 to the display circuitry (the output side of resistor 124 has Zener diode 126 connected therewith and capacitor 128 is connected at the input side of resistor 124).

The +5 volt power supply output from section 96 is provided through diode 130 connected to the collector of transistor 108 with diode 130 having resistor 131 connected therewith, with resistor 131 having capacitor 132 and Zener diode 134 to ground connected at opposite sides thereof.

The primary winding 105 of transformer 106 is also connected through resistor 136 to the base of transistor 138, the collector of which is connected to primary winding 140 (7 turns) of transformer 142 of power supply section 98. Secondary winding 144 of transformer 142 is connected with diode 146, the output of which is coupled through resistor 148 as the +30 volt DC output. Resistor 148 has a capacitor 149 at one side thereof to ground and Zener diode 150 to ground at the other side.

The −5 volt power supply is provided through winding 152 (7 turns) of transformer 142 connected through diode 153 and resistor 154, with resistor 153 having capacitor 155 to ground at one side and Zener diode 156 to ground at the other side (i.e., the output side).

As also indicated in FIG. 6, the output from batteries 56 is also coupled to low battery indicator circuitry 100. As shown, the +3 volt input from the batteries is coupled to pin 8 of integrating circuit 158 (for example an ICL8212CPA), is coupled through resistors 160 and 162 to input 2 of circuit 158, and is coupled through resistor 160 to input 3 of circuitry 158, with resistor 164 to ground also being connected to the junction of resistors 160 and 162. The low battery output indication is coupled from pin 4 of circuit 158 with light emitting diode (LED) 102 being a typical indicator to indicate, by constant energization of the LED that sufficient power is being supplied, and to include, by interrupted energization of the LED (i.e., by blinking of the LED) that low battery power is being sensed, as is conventional.

Turning again to TENS generator 60, a schematic diagram thereof is set forth in FIG. 7. As shown, mixer 68 is an integrated circuit having rate generator 62 and width generator 65 connected thereto, with rate generator 62 being coupled to input 1 through resistor 170 (the junction of which has a capacitor 172 to ground connected therewith). The width generator 65 input is coupled to pin 3 through resistor 174 (with capacitor 176 being connected between inputs 2 and 3 of unit 68).

Mixer 68 receives the high frequency input from high frequency generator 70, which as shown in FIG. 7, is connected to pin 11 of mixer 68 through resistor 178 and to pin 9 through diode 180 (having resistor 182 to ground connected therewith). Pin 11 of mixer 68 also has a capacitor 184 to ground connected therewith, and pin 12 is connected to pin 13 through resistor 186, with pin 13 also having capacitor 188 to ground connected therewith. As shown, pin 12 is also connected to isolation amplifier 73, the collector of which is connected through resistor 190 to the +5 volt power supply, and diode 192 is connected between pins 6 and 9 of mixer 68.

The output from mixer 68 is coupled from pin 8 to the base of amplifier 76 through resistor 194. The collector of amplifier 76 has the output coupled therefrom through resistor 196 to potentiometers 80 and 82 and to variable resistor 86 (providing DC offset), and the output from the wipers of potentiometers 80 and 82 is commonly coupled to constant current generators 88 and 90, and, more particularly, is coupled to the bases of transistors 198 and 200, the emitters of which are connected to the +30 volt power supply through resistor 202 (with the power supply having a bypass capacitor to ground 204 connected therewith).

The output from transistor 198 is coupled through resistor 206 and lead 36a to electrode 38a, while the output from transistor 200 is coupled through resistor 208 and lead 36c to electrode 38c. Return electrode 38b is coupled through lead 36b and resistor 92 to ground, while electrode 38d is connected through lead 36d to ground.

FIG. 8 illustrates the stimulator (i.e., TENS unit 60) applying the output signals to the electrodes, with outputs therefrom being utilized to drive displays 32 and 34, display 32 being the digital display and display 34 being the bar graph display. The output taken from electrode 38b is commonly coupled to analog-to-digital (A/D) voltage display driver 212 to drive digital unit 32 and to analog-to-digital (A/D) bar display driver 214 to drive the bar display, with each driver having a calibration potentiometer (potentiometers 216 and 218, respectively, as shown in FIG. 8) connected therewith.

Bar graph display driver 214 is shown in greater detail in FIG. 9. As shown, the input is coupled through variable resistor 222 to pin 5 of analog-to-digital (A/D) convertor and voltage comparator unit 224 (for example an LM3914) with pin 5 being connected to ground through resistor 226, and pins 6 and 7 being connected to ground through resistor 228. Unit 224 operates as a voltage comparator such that increases in voltage above predetermined values cause each output to be successively energized. The outputs from unit 224 are coupled through resistors 230 back to pins 3 and 9 of unit 224, with the outputs also being coupled to exclusive—or circuits 232, 234 and 236 (for example utilizing three Z4686 integrated circuits). The outputs from circuits 232, 234 and 236 are coupled to high voltage driver circuits 238 and 240 (for example ULN2023 integrated circuits) having AC outputs directly coupled to control the display (liquid crystal display) represented by the bars of display 34. Resistors 242 are utilized to couple the +50 volt power to circuits 238 and 240.

In addition to a pulsed DC signal coupled to the electrodes, it is also possible to couple an AC signal to the electrodes, as well as a pulsed DC signal followed by an AC signal or various other combinations of such signals, and different ones might be preferred over the others for use in different situations, although it is now felt that the pulsed DC signal followed by an AC signal is preferred. As shown in FIG. 10 for electrodes 1, to accomplish switching from AC to DC, double-pole, double-throw switch 246 is provided having switching sections 248 and 250 with switching section 248 connecting the output from transistor 198 to electrode 38a when in the DC position and connecting the output from transistor 198 to electrode 38a through capacitor 252 when in the AC position. Switching section 250 is not utilized when in the DC position, but in the AC position connects the output from transistor 198 to electrode 38b through resistor 254. If dual electrodes are utilized, switching would be accomplished in the same manner. For switching between pulsed DC and AC, switch 246 could be manually actuated, but preferably is automatically actuated by means of timer 256. For best operation, it is now felt that the pulsed DC signal should be applied for a period ranging from less than a minute to five minutes, and preferably from one to two minutes, followed by thereafter applying the AC signal.

FIG. 11 depicts TENS circuitry unit 60 having an output coupled through 100 μFd capacitor 258 to a typical 1000 ohm load resistor 260 (between electrodes 38a and 38b). When so connected and utilized in DC position for pulsed DC, a typical waveform is shown in FIG. 12A with an enlarged portion (indicated as 12B in FIG. 12A) of the waveform being shown in FIG. 12B. In like manner, when utilized with an AC waveform, a typical waveform is shown in FIG. 12C with an enlarged portion (indicated as 12D in FIG. 12C) of the waveform being shown in FIG. 12C.

The apparatus can include an electrode-connection safety feature to assure proper connection and functioning of the electrode circuitry. As illustrated in FIG. 11, this feature is implemented by amplifier 262 connected to lead 36b, with the output of amplifier 262 being coupled to Schmitt trigger 264. The output of Schmitt trigger 264 is coupled to low frequency oscillator 266 which provides an output to bar graph display 34 to cause the bar graph display to flash, or blink, (i.e., be intermittently energized) when the electrodes are not properly connected in the circuit or are not properly positioned within the mouth of a patient to complete the circuit.

As also illustrated in FIG. 11, timer 256 may be connected to Schmitt trigger 264, if desired, so that the timer does not start operation until the electrodes are properly positioned.

In operation, the operator, such as the dentist, applies the electrodes inside the mouth of a patient to the gum or the like (the electrode may have a cover over the adhesive which is removed before application of each electrode to the gum or the like). The electrodes are self-adhering, and the leads from the electrodes are connected with the main unit of the apparatus. The apparatus is then turned on by switch 28 and the dentist selects (or predicts before turning switch 28 on) the threshold intensity level by moving slide bar actuator 30 to the desired position. The intensity level is displayed at digital display 32 and slide bar display 34, since at this point, remote controller slide bar actuator 26 is preferably at a minimum level.

If so connected, bar graph display 34 will blink if the electrodes are not properly connected, and digital display 32 will blink if a low battery level is sensed. After energization, the apparatus will continue to apply dental anesthesia electrically. The dentist will then perform necessary dental work, and, if needed, the patient during this period can increase the intensity level of the applied electrical signal by adjusting actuation 26 (the intensity level then selected will be displayed by digital display and bar graph display 34).

After the dental work is completed, the apparatus is turned off by switch 28, and the electrodes are removed by peeling each from the gum or the like.

As can be appreciated from the foregoing, this invention provides an improved dental anesthesia device which utilizes an electronic stimulator to provide an output that is applied to a patient through electrodes within the mouth of a patient to effectively preclude sensing of pain by the patient during treatment.

What is claimed is:

1. A dental anesthesia apparatus, comprising:
   generating means for generating an electrical output signal;
   intensity control means having an input and an output with said input being connected with said generating means to control the intensity of said electrical output signal, said intensity control means including first and second controllers connected in parallel with one another between said input and said output, said first controller being accessible to an operator of said apparatus for setting a threshold intensity of said electrical output signal independently of said second controller and said second controller being accessible to a patient for adjusting the intensity of said electrical output signal only in a range above said threshold intensity thereby assuring an operator controlled minimum intensity level for said output signal; and electrode means connected with said output of said intensity control means to receive said intensity controlled electrical output signal.

2. The apparatus of claim 1 wherein said generating means includes transcutaneous electronic nerve stimulating means.

3. The apparatus of claim 1 wherein said generating means includes means for providing at least one of a pulsed DC output signal offset to a fixed quiescent DC level above a zero volt reference, an AC output signal, and a combination of said pulsed DC output signal and said AC output signal.

4. The apparatus of claim 3 wherein said apparatus includes application means for controlling application of said output signal, and wherein said combination of output signals is provided by providing said pulsed DC output signal for a predetermined period of time and thereafter applying said AC output signal.

5. The apparatus of claim 4 wherein said application means includes means for causing said pulsed DC output signal to be applied for a time period of between about one to two minutes and said AC output signal to thereafter be applied so long as said apparatus remains then energized.

6. The apparatus of claim 1 wherein said apparatus includes a main unit having said generating means thereat, and wherein said first controller is positioned at said main unit and is accessible to said operator to select the threshold intensity of said electrical output signal applied to a patient.

7. The apparatus of claim 6 wherein said second controller is remotely positioned with respect to said main unit and is accessible to said patient for selection only of an intensity greater than said threshold intensity selected at said main unit by said operator.

8. The apparatus of claim 1 wherein said apparatus includes a main unit having said generating means thereat, wherein said second controller is remotely positioned with respect to said main unit and is accessible to said patient for selection of the intensity of said electrical output signal applied to said patient, and wherein said electrode means is connected to said main unit.

9. The apparatus of claim 1 wherein said electrode means includes an electrically conductive element in engagement with an electrical lead for applying said electrical output signal to a patient and an adhesive for releasably maintaining said conductive element inside the mouth of a patient.

10. The apparatus of claim 9 wherein said electrode means includes an insulating base having said electrical lead and conductive element maintained thereon.

11. The apparatus of claim 1 wherein said apparatus includes constant current generating means connected with said intensity control means for providing said electrical output signal to said electrode means.

12. The apparatus of claim 11 wherein said constant current generating means includes first and second constant current generators, and wherein said electrode means includes first and second pairs of electrodes with said first pair of electrodes being connected with said first constant current generator and said second pair of electrodes being connected with said second constant current generator.

13. The apparatus of claim 1 wherein said apparatus includes display means for displaying the selected intensity of said electrical output signal.

14. The apparatus of claim 13 wherein said display means includes at least one of a bar graph and a digital readout for indicating said intensity.

15. The apparatus of claim 1 wherein said apparatus includes safety means connected with said electrode means whereby an alarm is provided if said electrodes are not properly positioned for application of dental anesthesia to a patient.

16. In a dental anesthesia apparatus having electronic stimulation means for providing an electronic output signal, an electrode connected to said electronic stimulation means for applying said electronic output signal to the mouth of a patient, said electrode comprising:
an insulating base;
a conductive element maintained on said insulating base;
an electrical lead between said base and said conductive element with said lead being in electrically conductive relationship with respect to said conductive element; and
a hydrophilic adhesive layer having a central notch therein for positioning and maintaining said conductive element in engagement inside the mouth of a patient, said adhesive being positioned adjacent to said conductive element on said insulating base so that at least a portion of said conductive element remains exposed through said central notch in a manner such that said exposed portion of said conductive element can be in contact with a portion of the mouth of a patient when said conductive element is positioned therein.

17. The electrode of claim 16 wherein said base is a foam base.

18. The electrode of claim 16 wherein said conductive element is a conductive elastomer.

19. The electrode of claim 18 wherein said conductive element is carbon impregnated silicone.

20. The electrode of claim 18 wherein said adhesive layer effectively surrounds said elastomer to maintain said elastomer at the inside of the mouth of a patient.

21. A dental anesthesia apparatus, comprising:
a main unit having generating means for generating one of a pulsed DC electronic output signal that is offset to a fixed quiescent DC level above zero, an AC signal, and a combination of said pulsed DC signal followed by said AC signal;
intensity control means connected with said generating means to control the intensity of said electronic output signal, said intensity control means including a first controller at said main unit and accessible to an operator for independently setting a threshold intensity, and a second controller remotely positionable with respect to said main unit and accessible to a patient, said second controller being connected so that the intensity of said output signal can only be adjusted by said patient in a range above said threshold intensity set by said operator;
electrode means connected with said intensity control means to receive said intensity controlled electronic output signal with said electrode means including a n electrically conductive element connected with electrical lead means extending from said main unit, and adhesive means for releasably maintaining said conductive element within the mouth of a patient; and display means including at least one of a bar graph display and a digital display for indicating the intensity selected.

22. The apparatus of claim 21 wherein said apparatus includes application means for controlling the output signal provided by said generating means.

23. The apparatus of claim 22 wherein said provided output signal is said combined signal, and wherein said application means includes timing means for causing said pulsed Dc output signal to be provided for a period of about one to two minutes and for causing said AC output signal to be thereafter provided.

24. The apparatus of claim 22 wherein said display means includes at least said bar graph display and wherein said apparatus includes safety means connected with said electrode means and said bar graph display to sense improper connection of said electrode means and indicate the same on said bar graph display.

25. The apparatus of claim 22 wherein said display means includes at least said digital display, and wherein said apparatus includes low battery indicating means connected with a battery and said digital display to indicate a sensed low battery power condition at said digital display.

* * * * *